(12) United States Patent
Nier et al.

(10) Patent No.: US 6,576,594 B2
(45) Date of Patent: *Jun. 10, 2003

(54) WATER TREATMENT PROCESS

(75) Inventors: Thomas J. Nier, Corpus Christi, TX (US); Tosby L. Linn, Corpus Christi, TX (US)

(73) Assignee: Bay Chemical and Supply Company, Odem, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/882,305

(22) Filed: Jun. 18, 2001

(65) Prior Publication Data

US 2002/0022059 A1 Feb. 21, 2002

Related U.S. Application Data

(60) Continuation-in-part of application No. 09/055,205, filed on Apr. 6, 1998, now Pat. No. 6,248,369, which is a division of application No. 08/744,742, filed on Oct. 28, 1996, now abandoned.

(51) Int. Cl.$^7$ .................. A01N 59/02; A01N 59/06; A01N 59/20; A01N 55/02; C02F 1/56
(52) U.S. Cl. .................. 504/152; 504/151; 424/630; 424/632; 424/633; 424/634; 424/635; 424/637; 424/638; 424/646; 424/647; 424/648; 424/682; 424/698; 514/499; 514/500; 514/502; 210/705; 210/723; 210/724; 210/728; 210/732; 210/735; 210/749; 210/753; 210/764
(58) Field of Search ............... 424/630, 632–638, 424/646–648, 682, 698; 504/151, 152; 514/499, 500, 502; 210/705, 723, 724, 728, 732, 735, 749, 753, 764

(56) References Cited

U.S. PATENT DOCUMENTS

| | | | | |
|---|---|---|---|---|
| 3,461,163 A | 8/1969 | Boothe | ...... | 564/296 |
| 3,844,760 A | 10/1974 | Nelson | ...... | 504/152 |
| 4,012,221 A | 3/1977 | Walker et al. | ...... | 504/151 |
| 4,049,545 A | 9/1977 | Horvath | ...... | 210/665 |
| 4,505,734 A | 3/1985 | Freedenthal et al. | ...... | 504/152 |
| 4,588,508 A | 5/1986 | Allenson et al. | ...... | 210/708 |
| 4,761,239 A | 8/1988 | Wardell | ...... | 210/727 |
| 4,882,070 A | 11/1989 | Wardell | ...... | 210/727 |
| 4,923,629 A | 5/1990 | Hasegawa et al. | ...... | 252/181 |
| 5,510,108 A | 4/1996 | Chouraqui | ...... | 424/408 |
| 5,541,150 A | 7/1996 | Garris | ...... | 504/152 |
| 6,120,698 A | 9/2000 | Rounds et al. | ...... | 252/181 |
| 6,248,369 B1 * | 6/2001 | Nier et al. | ...... | 424/637 |
| 6,420,312 B2 * | 7/2002 | Nier et al. | ...... | 504/152 |

FOREIGN PATENT DOCUMENTS

JP    63-240989    10/1988

OTHER PUBLICATIONS

Yin Chengqing et al., "Algal Bloom Control Study in Enclosure Experimental Ecosystems", Huanjing Kevue Xuebao, China, 1989.

Kirk–Othmer Encyclopedia of Chemical Technology, 4$^{th}$ Edition, vol. II, John Wiley and Sons, New York, 1994, pp. 61–67.

C.B. Muchmore, "Algae Control in Water–Supply Reservoirs", *Journal of American Water Works Association*, May 1978, pp. 273–278.

R. K. Raman, "Controlling Algae in Water Supply Impoundments", *Journal of American Water Works Association*, Aug. 1985, pp. 41–43.

I.H. Suffet et al., "Advances in Taste–and–Order Treatment and Control", American Water Works Association Research Foundation, 1995, pp. 39–43.

* cited by examiner

*Primary Examiner*—John Pak
(74) *Attorney, Agent, or Firm*—Nixon Peabody LLP; Daniel S. Song

(57) ABSTRACT

A method of controlling algae in a municipal water plant including the step of adding an algicide-flocculant solution including 25–50 wt % acidic flocculent, 0–10 wt % polymer flocculant aid, an algicide consisting essentially of copper having a concentration of 0.025–1.275 wt % in the form of a water soluble copper salt, balance water. The algicide-flocculant solution may be added to the water via a clarifier of the water plant, a basin of the water plant, or a mixing chamber. The mixing chamber may be located within the clarifier, adjacent to the basin, or upstream of the clarifier and/or the basin.

21 Claims, No Drawings

WATER TREATMENT PROCESS

This application is a continuation-in-part of application Ser. No. 09/055,205, filed Apr. 6, 1998, now U.S. Pat. No. 6,248,369, which is a division of application Ser. No. 08/744,742 filed Oct. 28, 1996, now abandoned.

This invention is a process for treating raw water and producing potable water meeting accepted purity standards.

BACKGROUND OF THE INVENTION

Surface water from rivers, lakes or reservoirs is treated in a water plant to convert the surface water into water for human consumption meeting accepted purity standards. The processes used have been honed over the years to produce high quality potable water. Surface water which has not been chemically treated is referred to by the industry as raw water and is referenced as same herein.

The process for treating water includes passing raw water through the municipal water plant while treating the raw water as it passes through the water plant. Primary treatment to the raw water in a water plant occurs in a clarifier or a basin (also referred to as a settling basin) after a flocculant has been added to raw water. The flocculant causes particles suspended in the water to coagulate, subsequently growing in size and weight. A water plant clarifier is a large sized, usually round structure whereas a basin is usually rectangular. The flocculant is generally added to the raw water in a small mixing chamber referred to as the rapid mix or flash mixer, to facilitate thorough, uniform mixing with the raw water. Depending on the design of the water plant, this chamber may be placed or positioned in various locations. In particular, the mixing chamber may be provided within the clarifier such as in a centerwell clarifier or adjacent to a basin. In other water plant designs, the mixing chamber may be provided upstream of the clarifier or the basin. The clarifier or the basin is generally sized to provide sufficient residence time for the majority of the solids to drop out of suspension. When necessary, the flocculant may be added to the water being treated in the water plant anywhere along the transfer pipe which delivers raw water from the river, lake or reservoir to the water plant to increase the total reaction time for the flocculant. Water is then passed through sand filters, perhaps treated with activated carbon, chlorinated and possibly fluoridated before being delivered to water supply mains which transport the treated water to residences, businesses and industries.

One of the recurrent problems in water treatment plant operations is the growth of algae in the clarifier or in the basin and sand filters. Algae come in many types including filamentous algae, such as Cladaphora and Spirogyra, planktonic algae such as Microcystis and Anabaena, branched algae such as *Chara vulgaris* and Nitellam, swimming pool algae commonly referred to as black, brown and red algae and algae found in ponds such as Dictyosphaerium, Spirogyra, Oedogonium, Chlorococcum, Pithophora, Hyudrodictyon and Lyngbya. It is not uncommon to see a municipal water plant clarifier or basin with a beard of algae around its peripheral walls and filamentous algae growths several feet long.

As used herein, the term municipal water plant is intended to mean a water plant used in treating raw water and converting it to potable water for human consumption, regardless of whether the entity doing so is public or private.

Algae blooms have been noted to appear literally overnight under the right temperature and sunlight conditions and, if left untreated, will cause taste and odor problems in the finished waters. The problems caused by algae in municipal water plants are handled in a variety of ways by current treatment methods. The taste and odor problems which typically recur during periods of high summer temperatures and long daylight hours occur from detritus thrown off by algae in the clarifier or basin. Not all of this detritus is removed by sand filters. A portion of the detritus passing through the sand filters is converted in the final chlorination process to a family of chloro-organic compounds which contribute to the objectionable taste and smell that consumers complain about.

The standard treatment for controlling algae in municipal water plants is to scatter crystals of cupric sulfate pentahydrate, $CuSO_4 \cdot 5H_2O$, which is also known by its common name blue vitriol, into the water. Blue vitriol is commercially available in 50 pound bags having crystals ranging in size from fine (1/8") to large (1"). Scattering is done with a shovel, a scoop, or by hand. Ideally, the crystals dissolve in the water so the copper ion is present in the water. The soluble or active copper (II) ion kills algae because of its effect on chlorophyll which is a large porphyrin structure occurring either as blue-green chlorophyll-a or yellow-green chlorophyll-b. Both molecules have four centrally placed nitrogen atoms which complex a single magnesium atom. The magnesium removes carbon dioxide from the water and delivers it to the algae thus allowing photosynthetic growth. The soluble copper (II) ion replaces the magnesium by forming a stronger porphyrin complex, which does not bond with carbon dioxide. The algae die by virtue of its growth mechanism being squelched by a lack of carbon dioxide, in a process analogous to the chemical poisoning of hemoglobin in mammals. One of the inherent advantages of copper algicides is that algae cannot mutate or evolve to avoid its effect. No amount of evolution can prevent copper from displacing magnesium in the chlorophyll and no amount of evolution can cause the copper porphyrin to absorb carbon dioxide.

Disclosures of some interest are found in U.S. Pat. Nos. 3,844,760; 4,012,221; 4,505,734 and 5,541,150.

SUMMARY OF THE INVENTION

The above description of the prior art is an idealized situation but which has a number of practical problems and disadvantages, some subtle and some not so subtle. A substantial part of the blue vitriol does not dissolve because it is difficult to dissolve in water which is not acidic. Plainly put, blue vitriol crystals do not dissolve very well in pH 7, or more alkaline water. Since the incoming raw water most often has a pH of 7 or above, this causes the crystals to acquire a coating of copper hydroxide that inhibits dissolution of the blue vitriol crystals into the water. Thus, much of the copper sulfate is wasted and ends up in the settled sludge in its undissolved form. Consequently, only a small portion is consumed, as intended, by intimate bonding to the algae chlorophyll. In addition, scattering blue vitriol crystals does not produce uniform dosages of copper sulfate in the water. Instead, very high dosages will be found immediately down current from the crystals and little copper sulfate will be found elsewhere.

In this invention, a water soluble copper salt is dissolved in an aqueous acidified solution such as an acidic flocculant because many water soluble copper salts, and the preferred copper sulfate, are much more soluble in low pH water than in neutral to high pH water. The resultant algicide-flocculant solution in accordance with the present method can be delivered in a tank truck or by a tank rail car and off loaded into storage tanks.

In the manner previously described, the treating of raw water in accordance with the present invention includes the standard steps of passing raw water through the municipal water plant while treating the raw water as it passes through the municipal water plant. In this regard, it should be appreciated that water continually flows through the various parts of the water plant such as the clarifier and/or basin as it is being treated in the water plant. In accordance with the present invention, the algicide-flocculant solution as described in further detail below is metered into the raw water being treated at an injection point which allows thorough mixing of the algicide-flocculant solution with the raw water as it continually flows through the water plant and is treated therein. In this regard, the solution may be metered into the raw water as it passes through the clarifier via a mixing chamber in the centerwell, or as it passes through the basin via a mixing chamber adjacent to the basin. In other applications, the algicide-flocculant solution may be metered into the raw water somewhere upstream of the clarifier and/or the basin via a mixing chamber located upstream of the clarifier and/or the basin. Such a mixing chamber may include a rapid mix or a flash mixer both known in the art which facilitates thorough uniform mixing of the flocculant and copper algicide with the raw water being treated at the water plant. Of course, other methods or devices may also be used. Metering pumps are generally designed to deliver a predetermined, controlled amount of a liquid and their use enables delivery of the copper algicide with the flocculant in a simple and efficient manner. The turbulence of the water stream also provides thorough and uniform mixing of the algicide with the water, as contrasted to the prior art technique of scattering blue vitriol crystals. Efficient mixing of the copper algicide with the water provides low, uniform dosages of copper which is very desirable because little copper is wasted.

The copper solution provides copper (II) ions that displace the magnesium ion in chlorophyll to kill the algae in the clarifier or basin. The amount of copper in the algicide-flocculant solution is controlled; thus the amount of copper added to the raw water is also controlled and is maintained at low levels. The copper reacts with the magnesium in the chlorophyll molecules and, along with the dead algae, collects in the sludge in the bottom of the clarifier and/or the basin.

When using this invention, no blue copper crystals will be found in the settled sludge, which means that more of the copper has been put to its intended use of killing algae rather than being wasted. In addition, the amount of soluble copper ion passing through the clarifier or basin into the finished water will normally not exceed 0.1 ppm which is well below the 1.3 ppm standard required by the Lead and Copper Rule of the Environmental Protection Agency.

It is difficult to overstate the importance of low, uniform dosages of copper. For the algicide to be effective, copper (II) ions must come intimately close to the magnesium ion in the chlorophyll complex of substantially all of the algae cells. This can be accomplished with improved mixing and distribution of the algicide when it is combined with the flocculant as in this invention so the algicide-flocculant solution then being mixed with the water being treated at the water plant provides uniform dosage of the copper. Uniform dosages are the key to effectiveness while low concentrations reduce treatment costs.

In the past, a water plant has typically used a conventional flocculant, either with or without a polymeric flocculant aid. With the onset of a substantial algae bloom, attempts would be made to control the algae bloom using the prior art technique with less than satisfactory results. When facing a full grown algae bloom, the amount of copper in the algicide-flocculant solution of this invention would be at a relatively high level which will bring the algae bloom under control in a fairly short period. After the algae bloom is brought under control, the amount of soluble algicide will be reduced in subsequent batches of algicide-flocculant solutions and ultimately reduced to a lower level that is sufficient to keep algae growth suppressed. As will be appreciated by one of ordinary skill in the art, the subsequent batches of algicide-flocculant solution is not generally added to the same body of water already treated with the initial batch of the algicide-flocculant solution since water is continually flowing through the water plant as it is being treated in a continuous treatment process. Because the algae bloom is brought under control with the algicide-flocculant solution having the higher initial dosage of copper, the subsequent batches can have reduced dosages of copper to maintain this control as the water is continually processed through the water plant. A large proportion of the algicidal copper exits the treated water stream in the settled sludge and not with the finished water because it has been intimately bonded to the algae chlorophyll. The water is then passed through filters such as sand filters. In addition, the water may be further treated with activated carbon, chlorinated and possibly fluoridated before being delivered to water supply mains which transport the treated water to residences, businesses and industries.

An object of this invention is to provide an improved technique for treating algae in a municipal water plant.

A more specific object of this invention is to treat raw water with an algicide-flocculant solution which, drops particulates out of suspension and simultaneously controls algae in the clarifier, the basin, and/or the sand filters.

These and other objects and advantages of this invention will become more apparent as this description proceeds, reference being made to the appended claims.

DETAILED DESCRIPTION

The copper algicide of this invention is selected from water soluble copper salts. From a simple algicidal standpoint, almost any water soluble copper salt is suitable. From the standpoint of producing potable water, the choice is more limited because not all water soluble copper salts can economically be put into drinking water. Thus, the common choices for the water soluble copper salt are copper sulfate, copper chloride, copper nitrate and copper acetate. The selection will likely be based on the relative cost of copper salts. Copper sulfate is the preferred water soluble copper salt because it is the only one presently approved for use in municipal water plants; it is effective as a source of copper (II) ions; and, it is the least expensive of the possible candidates. The preferred form of copper sulfate is blue vitriol which is cupric sulfate pentahydrate.

The amount of blue vitriol in the algicide-flocculant solution varies between 0.1–5% by weight. The proportion of copper in blue vitriol is 25.45% by weight which means that the copper concentration in the algicide-flocculant solution varies from about 0.025–1.275% by weight. Preferably, the amount of blue vitriol in the algicide-flocculant solution is 0.1–1% by weight meaning that the active copper concentration in the preferred solution is about 0.025–0.25% by weight. The equivalent concentration of other soluble copper salts is found in Table I:

TABLE I

| Copper Salt | Copper Salt concentration necessary to produce 0.025% active Cu (II) | Copper Salt concentration necessary to produce 1.275% active Cu (II) |
| --- | --- | --- |
| $CuSO_4 \cdot 5H_2O$ | 0.10% | 5.0% |
| $CuCl_2 \cdot 2H_2O$ | 0.067% | 3.35% |
| $Cu(acetate)_2 \cdot H_2O$ | 0.078% | 3.93% |
| $Cu(NO_3)_2 \cdot 3H_2O$ | 0.095% | 4.75% |
| $Cu(NO_3)_2 \cdot 6H_2O$ | 0.116% | 5.82% |
| $CuSO_4 \cdot H_2O$ | 0.070% | 3.49% |

Accordingly, the concentration of the copper salts vary from about 0.05% to about 6% by weight in order to provide the desired range of active copper concentration.

As noted above, the copper concentration in the algicide-flocculant solution in accordance with the present invention is between 0.025–1.275 wt %. It has been found in one preferred embodiment, that an active copper concentration of 0.25–0.765 wt % in the algicide-flocculant solution may be needed to bring algae blooms under control.

As also previously described, in accordance with one embodiment of the present invention, the water may be treated by adding the algicide-flocculant solution in a series of batches preferably with progressively reduced copper concentration to effectively control the algae bloom. In this regard, initial batches of algicide-flocculant solution would have relatively high copper concentration such as approximately 0.38–1.275 wt %, or preferably 0.25–0.765 wt % for example, so that the algae die off substantially. Then, subsequent batches of algicide-flocculant solution preferably containing reduced amounts of active copper algicide are provided to further reduce the algae levels.

In this regard, the subsequent batches of algicide-flocculant solution may be about half the initial dose. Copper concentrations in the algicide-flocculant solution in the range of about 0.025–0.38 wt %, or preferably, 0.125–0.38 wt % are usually sufficient as a maintenance dose to keep algae under control and prevent the formation of algae blooms, even under the most trying conditions of temperature and sunlight. For instance, a second batch of the algicide-flocculant solution may have a copper concentration of less than about 0.38 wt % such as 0.125–0.38 wt %, and a third batch of the algicide-flocculant solution may have a copper concentration of about 0.125–0.25 wt %. As previously described, the subsequent batches of algicide-flocculant solution are not generally added to the same body of water already treated with the initial batch of the algicide-flocculant solution since water is continually flowing through the water plant or parts thereof such as the clarifier and/or the basin as it is being treated in the water plant but is added to the raw water continually flowing into the water plant. Again, the subsequent batches preferably have a reduced dosage of copper to maintain this control as the water is continually processed through the water plant.

Moreover, as previously noted, the algicide-flocculant solution may be metered into the raw water as it passes through the clarifier via a mixing chamber in the centerwell, or as it passes through the basin via a mixing chamber adjacent to the basin. In other applications, the algicide-flocculant solution may be metered into the raw water somewhere upstream of the clarifier and/or the basin via a mixing chamber located upstream of the clarifier and/or the basin. The water is then passed through filters such as sand or other appropriate media. In addition, the water may be further treated with activated carbon, chlorinated and possibly fluoridated before being delivered to water supply mains which transport the treated water to residences, businesses and industries. Because the water has been effectively treated and the algae controlled, the taste and odor problems associated with detritus thrown off by algae in the clarifier or basin are minimized.

The specific location or part of the water plant where the algicide-flocculant solution is metered into the water as it flows through and is treated in the water plant largely depends on the design and configuration of the water plant to which the present invention is applied. In this regard, it should be appreciated that in accordance with the present method, the algicide-flocculant solution as described in further detail herein below can be added to the raw water being treated at any appropriate location or part of the water plant and the above specific locations are merely provided to suggest locations for some commonly used water plant designs and configurations. However, it should further be noted that significant advantages are provided by adding the algicide-flocculant solution to the clarifier or upstream of the clarifier since algae growth can then be readily controlled downstream of the location at which the algicide-flocculant solution is added. For instance, by adding the algicide-flocculant solution to a mixing chamber such as a rapid mix located upstream of the clarifier, algae growth in the clarifier and/or the basin can be readily controlled. In addition, by adding the algicide-flocculant solution upstream of the clarifier and/or the basing, the algicide-flocculant solution would allow control of algae growth in the filter and any other part of the water plant further down stream in the water treatment process.

In order to make the algicide-flocculant solution as described, it is theoretically possible to add copper salt crystals in the proper proportion to an acidic flocculant solution and agitate the solution to dissolve the copper salt. In practice, this has not been efficient for a variety of reasons. The source of blue vitriol is crystals which require vigorous agitation to dissolve, such as occurs with a powered impeller. With aluminum sulfate as the flocculant, solubility is adversely affected by the common ion effect. It is accordingly much better to dissolve the copper salt in water and then mix the water soluble copper salt solution with the flocculant solution. Using copper sulfate as the algicide, one part blue vitriol is dissolved in two parts water making a nearly saturated copper sulfate solution.

In accordance with one embodiment, to prepare the water solution of the copper salt, a mixing tank is partially filled with water and a suitable mixer, such as a powered impeller, is used to agitate the water. Preferably, the water is heated with a suitable heater, such as an electrically powered immersion heater or preheated by conventional methods such as a water heater. The selected copper salt is taken from commercially available bags and the desired quantity added to the tank. Using blue vitriol, the water solution will initially be bluish but somewhat milky which is caused by partial formation of copper hydroxide. Continued stirring and complete dissolving of the blue vitriol will result in a clear blue color typical of copper sulfate solutions.

During the mixing process in accordance with one embodiment, the copper salt solution is acidified to a pH of no more than 5 and preferably in the range of 4–5. This may be accomplished by adding a small quantity of acidic flocculant solution into the tank, typical flocculent solution having a pH of about 2.5, which is about the same as lemon juice. Acidifying the solution prevents the formation of copper hydroxide so the copper salt completely dissolves and remains in solution. Acidifying the solution with the flocculant material is advantageous in that it avoids using a different acid material which, in the treatment of water for human consumption, might provide regulatory problems.

Suitable flocculants of this invention are aluminum sulfate, iron sulfate, iron chloride and mixtures thereof. Polymeric aluminum flocculants such as aluminum chlorohydrate, polyaluminum chloride, polyaluminum sulfate, and mixtures thereof may also be used. Preferably, but not necessarily, the flocculants are prepared in a nearly saturated solution. In a typical process, aluminum oxide is reacted with sulfuric acid to produce liquid aluminum sulfate, i.e. about 47–50% by weight aluminum sulfate in water. Iron sulfate, iron chloride, and the polymeric aluminum flocculants may be prepared by commonly known procedures, as is well known in the art. In this invention, the amount of flocculant in the algicide-flocculant solution varies between 25–50% by weight and preferably is 35–50% by weight.

The invention is also useable with polymer flocculant aids of any suitable type. Polymer flocculant aids are long chain, high molecular weight cationic materials, usually having molecular weights in the range of 20,000–800,000. Conventional flocculants, such as aluminum sulfate, iron sulfate, iron chloride, aluminum chlorohydrate and mixtures thereof, produce relatively small flocs which require relatively long residence times to settle out by gravity in the clarifier and/or the basin. The polymer flocculent aids cause these small flocs to agglomerate into larger particles that settle at faster rates, thereby allowing shorter residence times in the clarifier and/or the basin. The present standard polymer flocculent aids are high molecular weight quaternary amines such as diallyldimethylammonium chloride or dimethylamine epichlorohydrin which are commercially available from various domestic manufacturers such as Ciba Specialty Chemicals (previously known as CPS Chemical Company) of West Memphis, Ark. In this invention, the amount of polymer flocculant aid in the algicide-flocculant solution varies between 0–10% by weight but preferably is 0–5% by weight. In one embodiment, the polymer flocculent aid may be added to the flocculant prior to the addition of the water soluble copper salt solution.

Potable water treatment chemicals are typically delivered by tank truck to the water plant. In this invention, the flocculent, with or without the cationic polymer aid, and the acidified copper salt solution are thoroughly mixed in a processing vessel or tank by agitation, air mixing or a recirculating pump. The complete homogenous mixture is then loaded into the tank truck or trailer for delivery to the water plant. In an alternate production method, the flocculant, with or without the cationic polymer aid, is simultaneously loaded with the acidified copper salt solution into the tank of a tank truck or a trailer. Final mixing occurs during transport, caused by agitation of the liquid contents due to movement of the truck/trailer.

The algicide-flocculant solution, with or without the polymeric flocculant aid, is added to the raw water using conventional metering equipment to deliver sufficient flocculent to coagulate the particulates in the raw water. As previously described, the algicide-flocculant solution as described can be metered into the raw water via the clarifier, the basin, or via a mixing chamber provided upstream of the clarifier and/or the basin, or any other appropriate location in the water plant to control algae growth.

In accordance with one embodiment, nearly saturated flocculant is added to the raw water in the range of 20–60 ppm, an average value being about 30 ppm. Because incoming raw water contains very little soluble copper, the active copper concentration in the clarifier and/or the basin is due almost entirely to the copper algicide combined with the flocculant. Thus, the treated water may have a copper concentration in the range of approximately 0.025–0.764 ppm.

Examples of how the algicide-flocculant solution can be prepared and/or used in accordance with the present invention to treat water include:

EXAMPLE 1

Approximately 55 gallons of water such as tap water are added to a mix tank. The water is then heated slightly using an electric immersion heater. 220 pounds of commercially available blue vitriol crystals are added to the mix tank and agitated vigorously with a powered impeller. During the mixing process, the aqueous solution is acidified and mixing continues until the blue vitriol crystals are completely dissolved, producing a clear blue liquid. A processing vessel or tank is filled with 4000 gallons of 47–50 wt % aluminum sulfate solution with no polymer flocculent aid. The copper sulfate solution is then transferred into the processing vessel or tank containing the aluminum sulfate. This produces a solution of ½% by weight copper sulfate, 45–47 wt % aluminum sulfate, balance water. Upon delivery to the water plant, the solution is transferred to a storage tank. It is then metered at about 30 ppm to a rapid mix where thorough uniform mixing occurs with the incoming raw water to flocculate particulates in the water and kill algae in the clarifier or the basin. In this example, the ½ wt % solution can be used as a maintenance dosage to prevent recurrence of the algae bloom after the algae bloom is brought under control with a higher concentration solution, such as 1 wt %.

EXAMPLE 2

440 pounds of blue vitriol crystals are thoroughly dissolved in 110 gallons of acidified water. The copper sulfate solution is added to 4000 gallons of 48–50 wt % aluminum sulfate to produce a 1 wt % copper sulfate solution. The algicide-flocculant solution is metered into the incoming raw water at a dosage of about 30 ppm.

EXAMPLE 3

440 pounds of blue vitriol crystals are thoroughly dissolved in 110 gallons of acidified water. The copper sulfate solution is added to a 4000 gallon mixture of 41 wt % liquid alum and 5 wt % cationic polymeric flocculant aid, to provide a 1 wt % copper sulfate solution having 0.25 wt % active copper. The algicide-flocculant solution is metered into the incoming raw water at a dosage of about 25 ppm.

EXAMPLE 4

300 pounds of cupric chloride dihydrate crystals are fully dissolved in 110 gallons of acidified water. This copper chloride solution is added to a 4000 gallon mixture of 46 wt % aluminum sulfate and 1 wt % cationic polymeric flocculant aid, to make a 0.68 wt % copper chloride solution having 0.25 wt % active copper.

EXAMPLE 5

490 pounds of blue vitriol crystals are completely dissolved in 110 gallons of acidified water. This copper sulfate solution is added to 3700 gallons of 38–42 wt % liquid ferric sulfate, balance water, to make a 1 wt % copper sulfate solution having 0.25 wt % active copper.

EXAMPLE 6

245 pounds of blue vitriol crystals are thoroughly dissolved in 110 gallons of acidified water. This copper sulfate solution is added to a 3700 gallon mixture of 38 wt % ferric sulfate and 2 wt % cationic polymeric flocculant aid, to produce a 0.5 wt % copper sulfate solution having 0.125 wt % active copper.

EXAMPLE 7

335 pounds of copper chloride dihydrate are fully dissolved in 110 gallons of acidified water. The copper chloride solution is added to 4100 gallons of 34–37 wt % liquid ferric chloride, to make a 0.68 wt % copper chloride solution having 0.25 wt % active copper.

EXAMPLE 8

2200 pounds of blue vitriol crystals are thoroughly dissolved in 550 gallons of acidified water. The copper sulfate solution is added to a 3475 gallon mixture of 25 wt % liquid alum, 10 wt % cationic polymeric flocculant aid, balance water, to provide a 5% copper sulfate solution having 1.275 wt % active copper.

It is hard to exaggerate the effectiveness of the algicide-flocculant treatment of this invention in combating algae growth. For example, in one application in South Texas, the water plant had battled an algae bloom using the standard scattering of blue vitriol crystals into the clarifier for several months. Numerous complaints of bad tasting and bad smelling water were received. Upon using a 1 wt % copper sulfate-aluminum sulfate solution of this invention, the bloom was over in a few days and complaints of bad taste and smell stopped.

Another more objective measure of the effectiveness of this invention is found by comparing copper concentrations in the clarified water versus the tap water. In the examples in Table II, a copper sulfate-aluminum sulfate solution has been metered into a municipal plant clarifier in accordance with one embodiment of this invention. Substantially no copper is present in the raw water so all of the copper in the clarifier is added by the algicide-flocculant solution of this invention. No free copper is accumulating in the clarifier sludge. In other words, the copper consumed in the clarifier is being used for its intended purpose, i.e. to control algae growth. Table II tabulates the results of trace copper analyses in tap and clarified water in several South Texas municipal water plants.

TABLE II

| Location | Date | Cu Conc. in clarifier water, mg/L | Cu Conc. in tap water, mg/L | Cu consumed in clarifier, mg/L | % Cu consumed in clarifier |
|---|---|---|---|---|---|
| Plant S | 10/08/96 | 0.035 | 0.011 | 0.024 | 66% |
| Plant L | 10/10/96 | 0.045 | 0.035 | 0.010 | 22% |
| Plant D | 10/10/96 | 0.026 | 0.018 | 0.008 | 31% |
| Plant O | 10/11/96 | 0.043 | 0.026 | 0.017 | 40% |

Upon reflection, it will be appreciated that the percentage of copper consumed in the clarifier averaged 40%. The copper present in the clarifier water is very dilute. For the copper ion to replace the magnesium ion in chlorophyll, the ions must come very close together, the exact distance being measured in Angstroms. Even so, a significant part of the copper added to the raw water in the clarifier by the technique of this invention is consumed and thus, is effective in combating algae.

In addition, it should also again be noted that although in the above described examples of Table II, the algicide-flocculant solution was added to the raw water via the clarifier, the solution can be added to the raw water at any appropriate location or part of the water plant depending on the design and configuration of the water plant to which the present invention is applied. It will also be appreciated that the reported percentage of copper consumed by the algae in the clarifier is understated because the measured copper concentration of the water in the clarifier is not necessarily the same as the copper added to the raw water in the clarifier. It is highly likely that some copper is consumed by algae in the clarifier before the water sample is taken that produced the results in Table II. In other words, because the sample point for the clarified water is downstream of the location at which the copper sulfate-aluminum sulfate solution is added to the water, a portion of the added copper will likely have been consumed before the sample was taken. Thus, the amount of reported copper in the clarifier is always less than the amount of copper added to the raw water. The result is that the reported percentage of copper consumed by the algae in the clarifier water is conservative.

A more accurate comparison of the effectiveness of this invention is to calculate the copper concentration fed to the raw water versus the concentration analyzed in the tap water since by calculating the difference of these Figures, direct determination of how much of the copper was consumed can be made. In the examples set out in Table III below, essentially all of the copper in the raw water is being provided by the copper sulfate-aluminum sulfate solution. It is noted that each plant was feeding a solution containing about 0.255 wt % copper at a rate which was recorded at the time of sampling the clarified and tap water. For example: Plant E was feeding 25 mg/L of a copper sulfate-aluminum sulfate solution which delivered 25 mg/L×0.00255=0.064 mg/L of copper.

Table III tabulates the results of trace copper consumption in several South Texas municipal water plants.

TABLE III

| Location | Date | Cu Conc. fed to raw water, mg/L | Cu Conc. in tap water, mg/L | Cu consumed in clarifier, mg/L | % Cu consumed in clarifier |
|---|---|---|---|---|---|
| Plant E | 11/14/96 | 0.064 | 0.017 | 0.047 | 73% |
| Plant B | 07/01/97 | 0.114 | 0.015 | 0.099 | 87% |
| Plant P | 07/08/97 | 0.153 | 0.029 | 0.124 | 81% |

As can be seen, the copper consumption results in Table III averaged approximately 80%, which indicates that a relatively high percentage of the copper is being consumed by the algae, as intended. The difference between copper absorption data in Table II discussed previously versus that of Table III above stems from the complete mass balance being used in the latter (Table III), which compared the exiting copper concentration and the added copper concentration. Such a high percentage of copper consumption as provided by the embodiment of the present invention is much greater than that which can be attained using conventional methods of dispersing blue vitriol crystals into the water. In this manner, the present invention provides a very effective water treatment process.

Although this invention has been disclosed and described in its preferred forms with a certain degree of particularity, it is understood that the present disclosure of the preferred forms is only by way of example and that numerous changes in the proportion of the materials and the details of mixing and use may be resorted to without departing from the spirit and scope of the invention as hereinafter claimed.

We claim:

1. A method of controlling algae in a municipal water plant, comprising the steps:
passing raw water through the municipal water plant while treating the raw water as the raw water passes through the municipal water plant; and
adding an effective amount of an algicide-flocculant solution to the raw water as the water passes through the municipal water plant, where the algicide-flocculant solution is mixed substantially uniformly with the water, wherein (i) the algicide-flocculant solution comprises 25–50 wt % acidic flocculant, 0–10 wt % polymer flocculent aid, an algicide consisting essentially of copper having a concentration of 0.025–1.275 wt % in the form of a water soluble copper salt, balance water, and (ii) said effective amount of the algicide-flocculant solution is an amount sufficient to kill algae in the water and to coagulate and/or flocculate particulates in the water that is being treated.

2. The method of claim 1, wherein the water soluble copper salt is selected from the group consisting of copper sulfate, copper chloride, copper nitrate and copper acetate.

3. The method of claim 1, wherein said step of adding an effective amount of an algicide-flocculant solution to the water is a step of adding an effective amount of a first batch of an algicide-flocculant solution in response to an algae bloom and the algicide-flocculant solution in the first batch comprises 25–50 wt % acidic flocculant, 0–10 wt % polymer flocculant aid, an algicide consisting essentially of copper having a concentration of 0.25–1.275 wt % in the form of a water soluble copper salt, balance water, and further comprising the step of subsequently adding, after the algae bloom has subsided in response to the first batch of the algicide-flocculant solution, an effective amount of a second batch of the algicide-flocculant solution into the water and substantially uniformly mixing the second batch of the algicide-flocculant solution with the water, the second batch of the algicide-flocculant solution comprising 25–50 wt % acidic flocculant, 0–10 wt % polymer flocculant aid, an algicide consisting essentially of copper having a concentration that is substantially less than the copper concentration in the first batch of the algicide-flocculant solution, balance water, wherein the effective amount of the second batch of the algicide-flocculant solution is an amount sufficient to further control algae and coagulate and/or flocculate particulates in the water.

4. The method of claim 3, further comprising adding, after said further control of algae has been obtained with the second batch of the algicide-flocculant solution, an effective amount of a third batch of an algicide-flocculant solution to the water and substantially uniformly mixing the third batch of the algicide-flocculant solution with the water, the third batch of the algicide-flocculant solution comprising 25–50 wt % acidic flocculant, 0–10 wt % polymer flocculant aid, an algicide consisting essentially of copper having a concentration that is substantially less than the copper concentration in the second batch of the algicide-flocculant solution, balance water, wherein the effective amount of the third batch of the algicide-flocculant solution is an amount sufficient to keep algae under control.

5. The method of claim 4, wherein the copper concentration in the first batch is 0.38–1.275 wt %, the copper concentration in the second batch being less than about 0.38 wt %, and the copper concentration in the third batch is in the range of about 0.125–0.25 wt %.

6. The method of claim 4, wherein the copper concentration in the first batch is 0.25–0.765 wt %, and the copper concentration in the second batch is 0.125–0.38 wt %.

7. The method of claim 1, wherein the algicide-flocculant solution is added to the water via at least one of a clarifier and basin of the water plant.

8. The method of claim 1, wherein the algicide-flocculant solution is added to the water via a mixing chamber.

9. The method of claim 8, wherein the mixing chamber is provided at least one of within a clarifier and adjacent to a basin of the water plant.

10. The method of claim 8, wherein the mixing chamber is provided upstream of at least one of a clarifier and a basin of the water plant.

11. A method of controlling algae in a municipal water plant, comprising the steps of:
pre-mixing an algicide-flocculant solution comprising 25–50 wt % acidic flocculant, 0–10 wt % polymer flocculant aid, an algicide consisting essentially of copper having a concentration of 0.025–1.275 wt % in the form of a water soluble copper salt, balance water;
passing raw water through the municipal water plant while treating the raw water as the raw water passes through the municipal water plant; and
adding an effective amount of the pre-mixed algicide-flocculant solution to the raw water, where the pre-mixed algicide-flocculant solution is mixed substantially uniformly with the incoming raw water, said effective amount of the algicide-flocculant solution being an amount sufficient to kill algae in the clarifier and to coagulate and/or flocculate particulates in the raw water that is being treated.

12. The method of claim 11, wherein the water soluble copper salt is selected from the group consisting of copper sulfate, copper chloride, copper nitrate and copper acetate.

13. The method of claim 11, wherein a first batch of the premixed algicide-flocculant solution with a copper concentration of 0.25–1.275 wt % is added to the water in response to an algae bloom to thereby obtain subsidence of the algae bloom.

14. The method of claim 13, further comprising the step of subsequently adding, after the algae bloom has subsided in response to the first batch of the algicide-flocculant solution, an effective amount of a second batch of the algicide-flocculant solution to the water and substantially uniformly mixing the second batch of the algicide-flocculant solution with the water, the second batch of the algicide-flocculant solution comprising 25–50 wt % acidic flocculant, 0–10 wt % polymer flocculant aid, an algicide consisting essentially of copper having a concentration that is substantially less than the copper concentration in the first batch of the algicide-flocculant solution, balance water, wherein the effective amount of the second batch of the algicide-flocculant solution is an amount sufficient to further control algae and coagulate and/or flocculate particulates in the water that is being treated.

15. The method of claim 14, further comprising adding, after said further control of algae has been obtained with the second batch of the algicide-flocculant solution, an effective amount of a third batch of an algicide-flocculant solution to the water and substantially uniformly mixing the third batch of the algicide-flocculant solution with water, the third batch of the algicide-flocculant solution comprising 25–50 wt % acidic flocculant, 0–10 wt % polymer flocculant aid, an algicide consisting essentially of copper having a concentration that is substantially less than the copper concentration in the second batch of the algicide-flocculant solution, balance water, wherein the effective amount of the third batch of the algicide-flocculant solution is an amount sufficient to keep algae under control.

16. The method of claim 15, wherein the copper concentration in the first batch is 0.38–1.275 wt %, the copper concentration in the second batch is substantially less than about 0.38 wt %, and the copper concentration in the third batch is in the range of about 0.125–0.25 wt %.

17. The method of claim 15, wherein the copper concentration in the first batch is 0.25–0.765 wt %, and the copper concentration in the second batch is 0.125–0.38 wt %.

18. The method of claim 11, wherein the algicide-flocculant solution is added to the water via at least one of a clarifier and a basin of the water plant.

19. The method of claim 11, wherein the algicide-flocculant solution is added to the water via a mixing chamber.

20. The method of claim 19, wherein the mixing chamber is provided at least one of within a clarifier and adjacent to a basin of the water plant.

21. The method of claim 19, wherein the mixing chamber is provided upstream of at least one of a clarifier and a basin of the water plant.

* * * * *